United States Patent [19]

Shanley

[11] 4,103,681

[45] Aug. 1, 1978

[54] TILTING TRACTION APPARATUS

[76] Inventor: Bernard J. Shanley, 1241 Garden Ave., Roseville, Minn. 55113

[21] Appl. No.: 721,977

[22] Filed: Sep. 10, 1976

[51] Int. Cl.[2] .................................................. A61F 5/00

[52] U.S. Cl. ........................................ 128/71; 128/74; 128/75

[58] Field of Search ........................ 128/73, 71, 74, 70, 128/75, 69; 272/144, 142, 138, 134; 269/323, 328

[56] References Cited

U.S. PATENT DOCUMENTS

| | | | |
|---|---|---|---|
| 540,939 | 6/1895 | Barton | 128/74 |
| 1,079,795 | 11/1913 | Naysmith | 128/73 |
| 1,092,435 | 4/1914 | Dorrance | 128/74 |
| 1,804,441 | 5/1931 | Silva | 128/75 |
| 2,533,273 | 12/1950 | MacGregor | 272/58 |
| 2,690,175 | 9/1954 | Daughtry | 128/71 |
| 2,976,868 | 3/1961 | Weissenberg | 128/71 |
| 3,060,925 | 10/1962 | Honsaker et al. | 128/25 R |
| 3,081,085 | 3/1963 | De Girolamo | 272/58 |
| 3,152,802 | 10/1964 | Heisler et al. | 272/33 |
| 3,238,936 | 3/1966 | Siedentop | 128/71 X |
| 3,388,700 | 6/1968 | Mountz | 128/24 |
| 3,522,802 | 8/1970 | Morton | 128/71 X |
| 3,568,669 | 3/1971 | Stites | 128/71 |
| 3,570,479 | 3/1971 | Horn | 128/71 |
| 3,589,358 | 6/1971 | Megal | 128/71 |
| 3,685,511 | 8/1972 | Alvarez | 128/57 |
| 3,741,200 | 6/1973 | Morin | 128/71 |
| 3,771,518 | 11/1973 | Greissing | 128/71 |
| 3,960,146 | 6/1976 | Albrecht | 128/75 |

*Primary Examiner*—Robert W. Michell
*Assistant Examiner*—Michael H. Thaler
*Attorney, Agent, or Firm*—Merchant, Gould, Smith, Edell, Welter & Schmidt

[57] ABSTRACT

A tilting traction table primarily for out-patient use having a platform hinged to a base. The platform is sized to support a patient from his knees upward, with a patient's lower legs extending over a first end of the platform. Apparatus, operable by hand or wrist action of the patient, is provided for controllably tilting the platform relative to the base, for lowering the patient's head relative to his knees, applying traction-like forces to the patient's back. An inclined ramp portion of the platform near its first end elevates the knees of the patient relative to the general plane of the platform. A belt attached to the platform near the first end thereof by an adjustable strap, is configured for securing the patient's hips against longitudinal movement along the platform when the platform is tilted, but enables lateral movement of the patient's hips during the traction process, for maximizing his comfort. A slide enhancing member is provided for insertion between the patient and the platform surface to provide ready slippage therebetween during a traction treatment. The inclined ramp portion may be slightly contoured to provide added comfort and retain engagement of the patient's legs.

9 Claims, 6 Drawing Figures

TILTING TRACTION APPARATUS

BACKGROUND OF THE INVENTION

This invention relates broadly to traction tables for treating patients with back injuries or other back problems including posture deficiencies. More particularly, the invention is directed toward traction tables that are manually operated by the patient while the patient is undergoing treatment.

The prior art traction devices include those in which the patient rests on a flat support surface while a weight attached to the patient's legs applies the traction force. Such devices include complex apparatus for attaching the weights to the patient, including pulley and cable structures. Such devices are particularly cumbersome when used on an out-patient basis in the home. Additionally, the patient while being treated, is unable to adjust the tension in accordance with his individual needs.

Tilting traction tables that utilize the patient's weight to apply the tension are also known in the prior art. Typically, in such devices, the patient reclines on a flat support surface and is secured to the table about the ankles and/or waist. Such traction devices tend to apply undesirable pressure to the patient's legs as opposed to the application of the needed tension to the back area.

The present invention overcomes problems associated with the prior art in that it is a truncated traction table having a platform with a surface for supporting a patient from the knees upward while the patient's legs hang over the end of the platform. The patient is restrained on the table in part by the action of the back side of the knees gripping the platform end. The knees and thighs are slightly raised from the platform surface to relieve pressure on the thighs. The angular tilt of the apparatus is easily regulated by the patient during treatment to control the tension applied.

SUMMARY OF THE INVENTION

The present invention is a therapeutic traction table having a truncated platform pivotally hinged to a base. The platform has a surface for supporting the patient from the knees upward while the patient's legs extend over the end of the platform. An apparatus for tilting the platform is provided. In one embodiment, the platform surface has a substantially flat member for supporting the patient from the buttocks upward and an end portion with a surface that gradually slopes upward at an angle with respect to the plane of the substantially flat portion. The patient's legs hang over the end of the platform and the back of the knees grip the platform to partially restrain the patient on the table.

A belt is also provided as a primary means of restraining the patient on the table. The belt is placed about the patient's waist and secured to the platform typically at the platform raised member. To enable the patient to adjust the traction force a handwheel is secured to the platform along one side thereof. The handwheel operates the platform tilting mechanism through a large gear ratio such that minimal amount of effort is required to change the orientation of the platform.

The raised end member of the platform is provided with contoured depressions which receive the upper legs of the patient. Additionally, the platform may be padded or covered by a fabric or a vinyl material. The patient's back may have a tendency to stick to the fabric or vinyl, and therefore a covering is slidably attached to the substantially flat portion of the platform. The cover minimizes the frictional forces between the patient's back and the platform enabling the weight of the patient to have a significant effect in the application of tension to the patient's back.

In an alternative embodiment, the truncated platform is substantially flat along its entire length. A removable pad is placed at the end over which the patient's legs hang to slightly raise the patient's upper legs and knees from the platform surface. This structure achieves the same effect as the platform with a raised end portion in that undesirable pressure is removed from the patient's thighs and legs.

In one embodiment the apparatus for tilting the platform is a jack screw threaded into a bracket in the base and connected by a gear structure to the platform. As previously mentioned, the gear ratio between the rotatable handwheel and the jack screw is sufficiently great so that the platform orientation is easily adjusted by the patient being treated. It is contemplated that alternative means of tilting the table could be utilized, to include electric or hydraulic powered apparatus.

In each embodiment, the truncated platform may be provided with an extension normal to the plane of the substantially flat portion of the platform and extending downward at the platform end over which the patient's legs hang. The extension supports the patient's legs while the patient undergoes treatment.

The present invention, thus, is a traction table particularly adapted for out-patient use in the patient's home. The tension is applied simply by the patient's own weight while the patient is retained on a tilting platform by a belt and the gripping action of the patient's knees over the end of the platform. The thighs of the patient are raised slightly to eliminate undesirable thigh pressure while the patient is undergoing traction. The present invention provides the advantage of being self-operated and is easy to use by the patient either in a home or hospital environment. The patient is free to move his shoulders and body transversely on the platform to facilitate his therapy. These and other advantages of my invention will become apparent with reference to the accompanying drawings, description and claims.

DESCRIPTION OF THE PREFERRED EMBODIMENT

Figure 1:
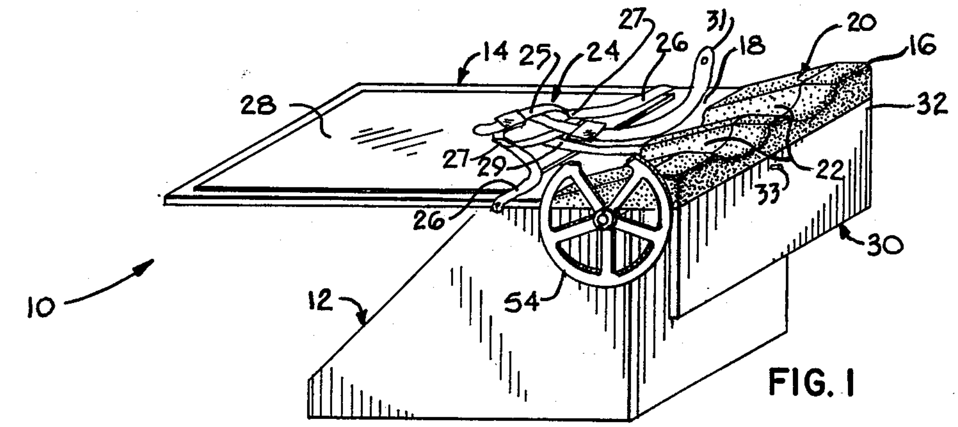
FIG. 1 is a view in perspective of the traction table incorporating my present invention.
Figure 2:
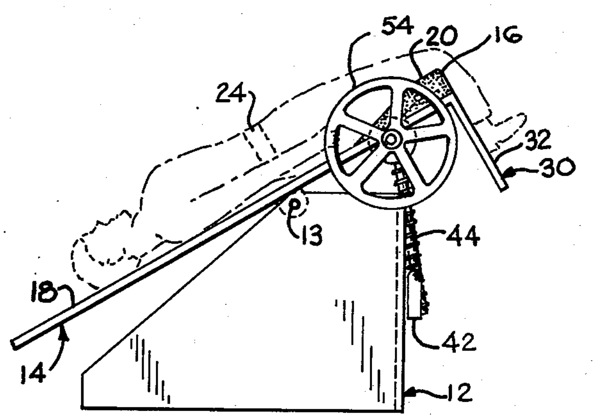
FIG. 2 is a side elevation of the traction table showing a patient in position on the table.

Referring to the drawing, wherein like numerals represent like parts throughout the several views, a tilting traction table designated generally as 10 is shown in FIG. 1. The table includes a base 12 to which is hinged at 13 a truncated platform 14. As shown in FIG. 2, the patient lies on the platform with the platform supporting the patient's body from his knees upward while the patient's legs extend over the platform end 16. In the preferred embodiment, the platform includes a first substantially flat supporting surface 18 and a second supporting surface 20 which extends upward from the first surface 18 at a slight angle. The patient's thighs are received within contoured depressions 22 in the surface 20. A belt 24 is provided to hold the patient against longitudinal translation along the table as the platform is tilted. Belt 24 has a portion 25 which grasps the patient about the waist. Straps 26 are secured to the sides of platform 14 and at their opposite ends have loops 27 through which portion 25 is threaded. Portion 25 can be adjusted for various size patients. A rear strap 29 is secured to portion 25 and attached to platform 14. A strap 31 also secured to portion 25 and platform 14 and is adjustable in length. FIG. 1 illustrates the attachment of strap 31 to a peg 33 as one method of attaching strap 31 to platform 14. It is within the scope of the present invention, however, to attach strap 31 in alternative manners and positions on platform 14. When the platform 14 is tilted to the position shown in FIG. 2, the patient is restrained against the gravitational pull on his body by the belt 24 and the grasp of the back of the patient's knees at the platform end 16. With the patient thus restrained tension is applied to the patient's back. Belt 24 as secured about the waist allows limited freedom of movement permitting the patient to alter his position on the platform if he becomes uncomfortable. Rails (not shown) may be provided along the sides of platform 14 to assist the patient in adjusting his position and to prevent the patient from accidentally slipping over the platform sides.

The angular slope of the surface 20 relieves any pressure or tension which may be applied to the patient's thighs. Thus, the tension force generated by the pull of gravity on the patient is pinpointed to the patient's back where the therapeutic treatment is needed. A portion of the therapeutic tension is therefore not wasted in the patient's thighs.

The platform 14 will normally have a fabric or vinyl covering. When the platform is tilted, there may be frictional forces between the patient's back and the platform covering that tend to decrease the effective applied tension. A sheet 28 is therefore placed in slidable contact with the substantially flat surface 18. The patient's upper body from approximately the buttocks region upward rests upon the slidable sheet 28. Thus, when the platform 14 is tilted about the hinge 13, the sheet 28 allows the patient to slide under the gravitational pull until the patient is restrained by the belt 24 and the natural gripping action of the backside of the patient's knees against the end 16.

The platform further includes the downward extension 30 which projects from the end of the raised surface 20 and platform end 16 and which is disposed in a plane normal to the plane of the substantially flat surface 18. The extension 30 provides a support surface 32 for the patient's legs as more specifically illustrated in FIG. 2.

Figure 3:
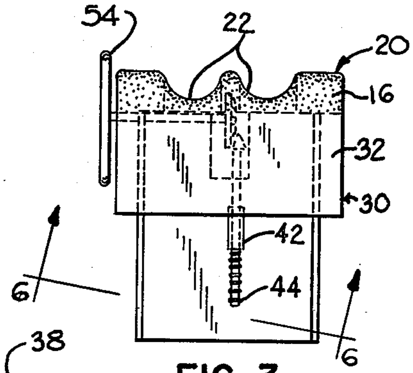
FIG. 3 is an end elevation of the table shown in FIG. 1.

FIG. 3 is an end view of the tilting traction device showing the contoured depressions 22 formed in the surface 20.

Figure 4:
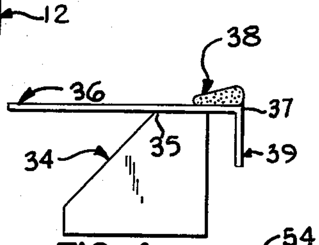
FIG. 4 is a side elevation of an alternative embodiment of the present invention.

In the alternative embodiment illustrated in FIG. 4, the tilting traction table includes a base 34 to which is hinged at 35 a platform 36. Disposed proximate the end 37 of the platform 36 is a removable pad 38 serving the same function as the inclined surface 20 of the table illustrated in FIG. 1. In other words, the patient's thighs rest on the pad 38 while the patient's knees naturally grasp the end of the pad and platform while the legs hang downward to be supported by the platform extenstion 39. As in the first embodiment, the pad 38 facilitates the application of the tension to the patient's back and eliminates undesirable and wasted tension on the patient's thighs.

Figure 5:
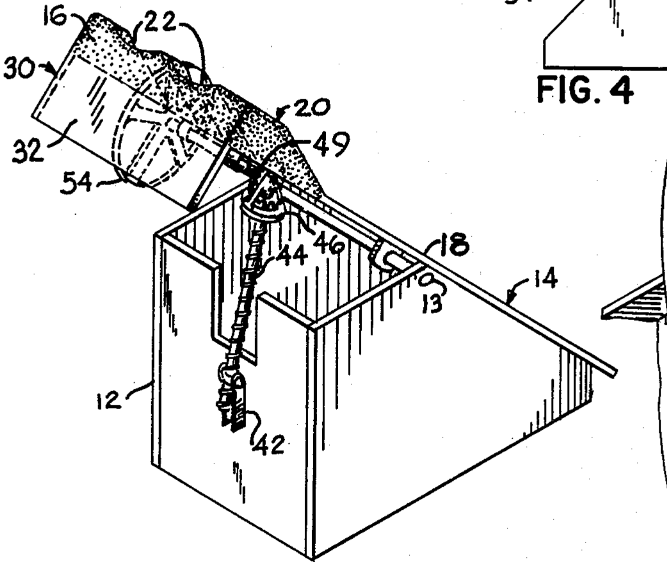
FIG. 5 is a view in perspective of the traction table in the raised position to illustrate the tilting apparatus of one embodiment of the present invention.
Figure 6:
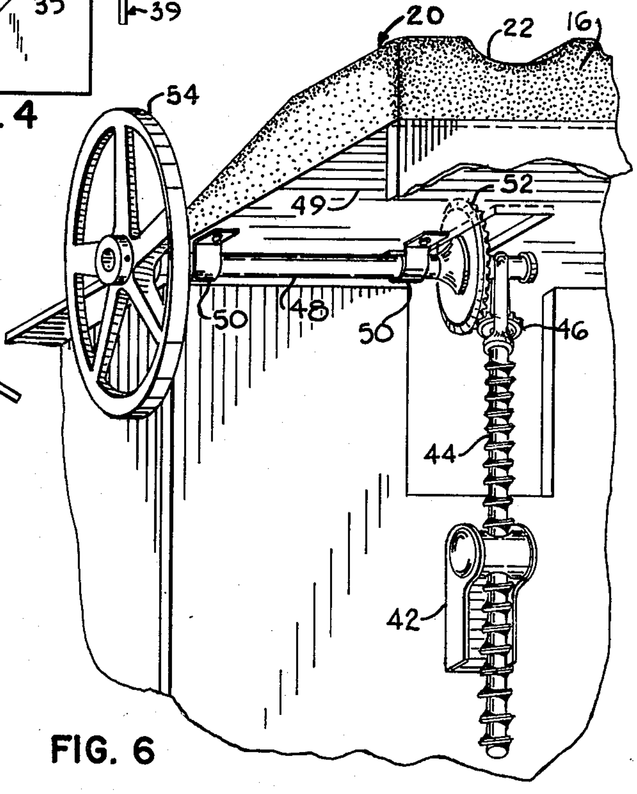
FIG. 6 is a partial fragmentary view in perspective of the traction table taken along line 6—6 of FIG. 3, illustrating in detail the tilting apparatus of one embodiment of the present invention.

On apparatus for raising and lowering the platform 14 about its hinge 13 will be described with particular reference to FIG. 2 and FIG. 5. Secured to the base 12 is a bracket 42 which threadably receives a jack screw 44. A gear 46 is formed integrally with the jack screw at its upper end. A shaft 48 is rotatably secured to the bottom surface 49 of the platform 14 by a pair of brackets 50. Attached to one end of the shaft is a large diameter gear 52 having teeth which mesh with the teeth of the gear 46. Connected to the opposite end of the shaft is a rotatable handwheel 54 disposed along the side of the platform and positioned so that the wheel is easily reached by the patient while the patient is undergoing treatment. The gear ratio of the gear 52 to the gear 46 is large enough so that a minimal amount of force must be exerted in rotating the handwheel to raise or lower the platform. Rotation of the handwheel is transmitted by the cooperating gears 52 and 46 into rotation of the jack screw 44. The jack screw thereby advances or retracts through the bracket 42 to raise or lower the platform.

While a handwheel and jack screw apparatus has been described and illustrated it is contemplated that electric or hydraulic powered devices are within the scope of the invention.

Thus, it can be appreciated from the above description, that the above invention provides a therapeutic traction table particularly adaptable for out-patient use in the home. The tension is easily adjustable by the patient undergoing treatment. The provision of a raised surface or pad upon which the patient's thighs rest eliminates undesirable and wasted tension applied to the patient's thighs. The tension is pinpointed to the back region and generated by the gravitational pull on the patient while the platform is in the tilted position.

I claim:

1. A tilting therapeutic traction table comprising:

(a) a base;

(b) a body support platform having first and second ends and a broad upper surface extending continuously between said first and said second ends and of a width sufficiently large to fully support the upper leg and torso portion of a human body, said platform being adapted for supporting a patient such that the head of a patient is disposed adjacent said first end and the legs of the patient from his knees downward hang freely over said second end of said platform, said platform being configured to further define a ramp-like surface disposed adjacent said second end of said platform, said surface being inclined upwardly in the direction from said first to said second ends and adapted to elevate the knees of a patient supported thereby above the general plane of said platform while fully supporting the thigh portion of the patient's legs, in a manner which contains the buttocks of the patient in engagement with said platform;

(c) hinge means for pivotally connecting said platform to said base, said hinge means being mounted intermediate said first end and said second ends of said platform;

(d) power transmission means suitable for direct operation by a patient lying on said platform, for tilting said platform about said hinge means to a degree proportional to the actuation input stimulus provided by the patient to the transmission means, said transmission means being operable to cause said first end of said platform to move downward while said second end of said platform moves upward and in a manner such that said first end of said platform is disposed increasingly relatively lower than said second end of said platform; and (e) restraining means adapted for engaging the hip portion of a patient lying on said platform for preventing movement of the patient against longitudinal translation of the patient along said platform in the direction from said second to said first end thereof when said platform is tilted.

2. A tilting traction table in accordance with claim 1, wherein said ramp-like surface has contoured depressions that are adapted to recieve a patient's thighs.

3. A tilting traction table in accordance with claim 1 wherein said restraining means further comprises:

(a) a belt adapted to be placed about the hips of the patient; and (b) an adjustable strap attaching said belt and to said platform adjacent said second end of said platform.

4. A tilting traction table in accordance with claim 1, further comprising sheet-like means slidably engaging said platform surface for reducing frictional forces between the back portion of a patient and said platform surface.

5. A tilting traction table in accordance with claim 4, wherein said platform surface is substantially covered with a vinyl material and wherein said sheet-like means comprises a plastic material of a type suitable for slidably engaging said vinyl covering material.

6. A tilting traction table in accordance with claim 1, wherein said tilting means further comprises:

(a) means secured adjacent said second end of said platform for raising and lowering said second end; and a handwheel operatively connected to said raising and lowering means and disposed along a side of said platform so as to be within easy reach of the hand of a patient reclining thereon, whereby rotation of said handwheel by the patient adjusts the tilt angle of said platform.

7. A tilting traction table in accordance with claim 6, wherein said raising and lowering means further comprises:

(a) a bracket attached to said base;

(b) a jack screw threadably received by said bracket and having one end thereof mounted to said platform, said jack screw upon rotation being longitudinally movable relative to said bracket;

(c) a shaft rotatably attached to said platform and secured to said handwheel for rotational movement therewith;

(d) a first gear secured to said shaft and rotatably movable therewith; and (e) a second gear integral with said jack screw and meshed with said said first gear, whereby rotation of said handwheel imparts rotational forces to said jack screw for raising and lowering said second end of said platform.

8. A tilting traction table in accordance with claim 1, further comprising: support means connected to said platform at said second end thereof and disposed in a plane normal to the general plane of said platform for supporting the calf portion of a patient's legs.

9. A tilting traction table in accordance with claim 1, wherein said ramp-like surface comprises a removable pad proximate said second end of said platform upon which the patient's thighs rest.

* * * * *